(12) United States Patent
Rochette

(10) Patent No.: US 8,070,732 B2
(45) Date of Patent: Dec. 6, 2011

(54) HOLDING DEVICE FOR LOCKING THE HEAD OF A SYRINGE PISTON ON A SYRINGE PUMP PUSHER

(75) Inventor: Francois Rochette, Apprieu (FR)

(73) Assignee: Fresenius Vial SAS, Brezins (FR)

( * ) Notice: Subject to any disclaimer, the term of this patent is extended or adjusted under 35 U.S.C. 154(b) by 473 days.

(21) Appl. No.: 11/814,133

(22) PCT Filed: Dec. 21, 2005

(86) PCT No.: PCT/EP2005/057032
§ 371 (c)(1),
(2), (4) Date: Feb. 6, 2008

(87) PCT Pub. No.: WO2006/074858
PCT Pub. Date: Jul. 20, 2006

(65) Prior Publication Data
US 2008/0262440 A1    Oct. 23, 2008

(30) Foreign Application Priority Data
Jan. 17, 2005    (FR) ...................................... 05 50132

(51) Int. Cl.
*A61M 5/315* (2006.01)
(52) U.S. Cl. ........................ 604/228; 604/131; 604/229
(58) Field of Classification Search .................. 604/131, 604/228, 229
See application file for complete search history.

(56) References Cited

U.S. PATENT DOCUMENTS

| | | | | |
|---|---|---|---|---|
| 4,791,832 A | * | 12/1988 | McCaw | 475/226 |
| 6,428,509 B1 | * | 8/2002 | Fielder | 604/154 |
| 6,569,127 B1 | * | 5/2003 | Fago et al. | 604/218 |
| 7,422,570 B2 | * | 9/2008 | Gerlach et al. | 604/154 |
| 2002/0049415 A1 | | 4/2002 | Fukuda | |
| 2002/0108832 A1 | * | 8/2002 | Kerr | 192/48.91 |
| 2004/0116893 A1 | | 6/2004 | Spohn et al. | |

FOREIGN PATENT DOCUMENTS

| | | |
|---|---|---|
| EP | 1066846 A1 | 1/2001 |
| EP | 1 195172 A2 | 4/2002 |
| EP | 1 279 410 A1 | 1/2003 |
| WO | 99/23398 A2 | 5/1999 |

OTHER PUBLICATIONS

International Search Report of PCT/EP2005/057032, date of mailing Apr. 6, 2006.

* cited by examiner

*Primary Examiner* — Kevin C. Sirmons
*Assistant Examiner* — Brandy C Scott
(74) *Attorney, Agent, or Firm* — Westerman, Hattori, Daniels & Adrian, LLP

(57) ABSTRACT

A holding device for locking the head of a syringe piston on a pusher has arms connected to respective pinions pivotable and translationally displaceable so that the corresponding arm is involved in the same motion between a rest position, in which the arms are closed and pressed against the pusher, and an open position, in which the arms are opened and remote therefrom, the translation is carried out prior to rotation during the movement toward the open position or in reverse order toward the rest position. The holding device also has a control member and means for converting a part of the control member movement by transmitting it to at least one pinion as a translation movement, which are translationally locked, and means for converting a part of the control member movement by transmitting it to at least one pinion as a rotation movement.

20 Claims, 4 Drawing Sheets

HOLDING DEVICE FOR LOCKING THE HEAD OF A SYRINGE PISTON ON A SYRINGE PUMP PUSHER

BACKGROUND ART

The invention relates to a holding device for locking the head of a syringe piston on a syringe pump pusher, the device being equipped with arms integral each with a pinion pivotable about its axis and movable in translation so as to drive the corresponding arm in a same movement between a rest position, in which the arms are "closed" and "pressed" against the pusher, and an open position, in which the arms are "opened" and "removed" from the pusher, the translation being performed before the rotation during the movement toward the open position, or in reverse order toward the rest position, the holding device further comprising a control member and means for converting a portion of the movement of the control member by transmitting it to at least one pinion in the form of a translation movement and means for converting a portion of the movement of the control member by transmitting it to at least one pinion in the form of a rotation movement.

Syringe pumps are often used in the medical field. These syringe pumps are constituted essentially by a device for immobilizing the cylinder of the syringe and a device for pushing the piston in the cylinder at a defined speed in order to supply the solution to the patient in a controlled manner. Further, it is preferable that the piston head be held against the pusher of the syringe pump to avoid a siphoning phenomenon. It happens sometimes that a depression forms downstream of the syringe. If the piston head is not held, there is a risk that the syringe will empty itself partially or completely and will thus supply the therapeutic solution to the patient at a much too high rate, which can have tragic consequences.

Various solutions have been proposed. For example, a hand-actuated holding device is known from document EP 1 279 410 A1, which device comprises an element mobile perpendicularly to the axis of the syringe. This mobile element is crescent-shaped with a V-shaped slot located in the inner arc of the crescent. By returning the mobile element against the pump housing, the edge of the piston head penetrates into the V-shaped slot, which then holds it against the pusher. This solution requires that the syringe head be aligned with the V-shaped slot of the mobile element.

In another common solution, the holding means are constituted by two arms. These arms, which are parallel to the syringe piston head, are mounted on pivoting axes that are parallel to the main axis of the syringe. When the syringe is placed in the syringe pusher, these arms are moved away from each other by pivoting them towards the outside, the piston head is placed against the pusher and the arms are released so that they return to a closed position, thus locking the piston head between them and the pusher.

By themselves, the arms can lock efficiently only syringe heads that have a defined thickness. In other words, the corresponding syringe pumps can be used only for a type of syringe or syringes from a single manufacturer, provided these syringes all have piston heads of the same thickness. Using these pivoting arms with thicker piston heads is not possible, as the arms cannot return to the closed position, and using them with thinner piston heads is dangerous, to the extent that even a very small siphoning effect can have serious consequences, in particular for solutions supplied at a very small rate.

Thus, arms exist that, not only pivot to open, but also carry out a translation movement along the axis of the syringe, so that they can adjust to the thickness of the piston head. Pushing on a lever triggers, first, the translation of these arms, which tends to move them away from the pusher, and then, a rotation movement of the arms, which tends to rotate them toward the outside while moving them away from each other. Once the piston head is placed against the pusher, the lever is released, the arms close again until they touch the syringe piston rod, then they move back toward the pusher until they touch the syringe piston head.

Such a holding device is known, for example, from document U.S. Pat. No. 6,428,509 B1. This device comprises a first pivoting mechanism that drives the arms in rotation and a second mechanism that drives the arms in translation. The pivoting mechanism is constituted essentially by three toothed wheels placed in series, the first toothed wheel transmitting the rotation movement of the actuating lever to a second toothed wheel, which is integral with the first arm, and the second toothed wheel transmitting in turn the rotation movement to a third toothed wheel integral with the second arm. In the translation mechanism, the rotation axes of the arms are pushed against an actuating plate that has on a protrusion on its other face. The actuating lever is integral with a control plate having a ramp, the protrusion of the actuating plate being supported on the control plate on the side of the ramp. When the lever pivots, this control plate moves until the protrusion slides against the ramp, thus triggering the downward movement of the actuating plate, and as a result, the translation of the arms away from the pusher. A hook locks the actuating plate when it reaches a certain distance, so that it is locked in this position without being able of moving backward again. When the actuating lever is moved back again, the arms close again. The hook that holds the actuating plate is released only during the last degrees of the pivoting movement of the lever, which enables the plate to move back toward the pusher, thus driving the arms along in the same movement. This device is particularly complex and requires a high number of parts.

Another holding device is known from document EP 1 066 846 A1, which device has arms that are pivotable and movable in translation. Each arm is mounted on an axis carrying each a toothed wheel equipped with a central radial groove. A toothed wheel, connected indirectly to an electric motor, is equipped with a central radial projection. This driving toothed wheel is intended to cooperate with the toothed wheel of the first arm, wherein the radial projection of the first toothed wheel projects into the central radial groove of the second. The driving toothed wheel cooperates also with a transmission toothed wheel that transmits the rotation movement of the driving wheel to the toothed wheel of the second arm. The toothed wheel of the second arm is positioned such that the radial projection of the driving toothed wheel also projects into its central radial groove, without meshing, however. Further, the driving toothed wheel is mounted on a ring equipped with an inner thread. The ring it itself mounted on a hollow rod having an outside thread and carrying at one of its ends a toothed wheel that cooperates with the motor. A rod having a flange at one of its ends has its free end projecting into the hollow rod, on the side opposed to the toothed wheel that cooperates with the motor. This rod is free in rotation in the hollow rod while being locked in translation. This assembly enables the driving toothed wheel to move in translation, thus driving the toothed wheels of the arms along in the same movement because the radial projection projects into the radial grooves of the toothed wheels of the arms. The translation movement is limited, on one side, by the toothed wheel that cooperates with the motor, and on the other side, by the flange. A group of springs promotes the translation of the driving wheel to the detriment of its rotation, which is triggered only when the driving wheel can no longer move in translation. Here also, the mechanism requires a high number of parts and its design is particularly complex.

Further, a holding device for the syringe cylinder is known from document US 2004/0116893 A1, which device provides, in one of its variants, three arms pivotable in a radial plane toward the center of the adapter. However, these arms are not movable in the axial direction.

SUMMARY OF THE INVENTION

The objective of the invention is thus to provide a mechanism according to the preamble, which has a simpler design and requires a lower number of parts. Another objective of the invention is to reduce the number of parts that must be subjected to a translation movement, so as to limit frictions and reduce the risk that some parts may become jammed.

This objective is reached with the device conform to the invention in which the means for converting and transmitting a portion of the movement of the control member into a translation movement of at least one pinion are locked in translation. The translation movement is thus limited to the pinions integral with the wheels, which reduces the risk of jamming.

In a preferred embodiment of the invention, the means for converting and transmitting a portion of the movement of the control member into a translation movement of at least one pinion and the means for converting and transmitting a portion of the movement of the control member into a rotation movement of at least one pinion are the merged. The number of parts is thus considerably reduced.

With a view at reducing the number of parts, it is preferable to make the pinions integral with the arms mesh with each other so that the rotation of one of the pinions causes the rotation in the opposite direction of the other pinion. This avoids the need to use an additional, intermediate pinion between the second pinion and the means for transmitting and converting the movement of the control member into a rotation movement of at least one arm to reverse the rotation movement with respect to the first pinion.

In order to make the pinions integral with the arms integral with each other in translation, it is preferable to equip one of the pinions with flanges on its lateral faces. Thus, when one of the pinions will be subjected to a translation movement, it will drive the other one along in the same movement in the direction of the arms moving away as well as in the return direction.

In a preferred embodiment of the invention, the means for converting and transmitting a portion of the movement of the control member into a translation movement of at least one pinion and the means for converting and transmitting a portion of the movement of the control member into a rotation movement of at least one pinion are constituted by a helical set of teeth. The helical conformation of the set of teeth makes it possible, when it is moved, to convey both a translation movement and a rotation movement to a set of teeth cooperating with it. For purposes of simplicity and economy of space, it is preferable that the helical set of teeth be mounted on a segment of pinion, and preferably oriented toward the inside of said pinion segment.

It is preferable to equip the pinion that cooperates with the converting and transmitting means with a helical set of teeth compatible with the helical set of teeth of the converting and transmitting means, and to have these two helical sets of teeth cooperate with each other. It is preferable that these two sets of teeth mesh directly with each other, so as to avoid additional intermediary parts.

For purposes of simplicity, it is preferable to equip the two pinions integral with the arms with reversed helical sets of teeth. In other words, the helical set of teeth of the pinion that cooperates with the set of teeth of the converting and transmitting means is used both for the transmission of the movement by the converting and transmitting means and for the transmission of the rotation movement to the second pinion integral with the second arm. In practice, a rotation movement of the helical set of teeth of the helical pinion segment caused by a rotation movement of the control member drives the pinion of the first arm, which cooperates with the helical pinion segment, into a translation and rotation movement. This pinion integral with the first arm transmits in turn the translation and rotation movement to the second pinion integral with the second arm.

This pinion integral with the first arm transmits in turn the translation and rotation movement to the second pinion integral with the second arm.

To avoid excessively high frictions while ensuring a balance between translation and rotation, the helical sets of teeth are preferably slanted at an angle of about 45°.

In order to ensure, in the opening direction, that the translation is performed before the rotation, and in the return direction toward the rest position, that the rotation is performed before the translation, pushing means are provided to push at least one of the pinions toward a remote position, these means being preferably constituted by a push spring, the action of these pushing means being preferably sufficiently strong to promote the translation movement of the pinions, as compared to their rotation movement, in the direction of opening and moving the arms away from each other. Thus, when the helical pinion segment pivots, the pinion meshing with it tends to perform preferably a translation movement under the action of the push spring, which drives the other pinion and thus the arms along in a translation movement. When this translation movement is completed, the helical pinion segment keeps on rotating, which brings about the rotation of the meshing pinion and thus the opening of the arms. When the control member is released, the push spring prevents, at first, the translation of the meshing pinion, thus forcing the meshing pinion to pivot, which drives the other pinion and causes a closing movement of the arms. When the arms reach the syringe piston rod or when their ends touch each other, the rotation of the meshing pinion is locked and only a translation movement is possible. This retraction movement continues until the arms reach the syringe piston head or the pusher of the syringe pusher.

In order to force the holding device to return automatically to the rest position or to a position as close as possible to this extreme position, return means are provided to return the holding device to the rest position, in which the arms are as closed as possible and as close to the pusher as possible. In order to ensure a satisfactory operation, the action of the return means is preferably stronger than the action of the pushing means, so that the device tends to return to the rest position when the actuating member is not in action.

The control member can be integral with an external control lever and/or with a transmission means controlled by the syringe pump. It is thus possible to actuate the holding device either manually or automatically.

It is preferable to provide means for allowing the control member to return to the rest position even if the holding device remains locked in an intermediary position between the open position and the rest position. This avoids damaging the holding device when the control member returns to the rest position while the holding device holds a piston head, and thus cannot return completely to the rest position.

BRIEF DESCRIPTION OF THE DRAWINGS

An example of embodiment of the invention is described below with reference to the figures showing.

DETAILED DESCRIPTION OF PARTICULAR EMBODIMENTS

Figure 1:
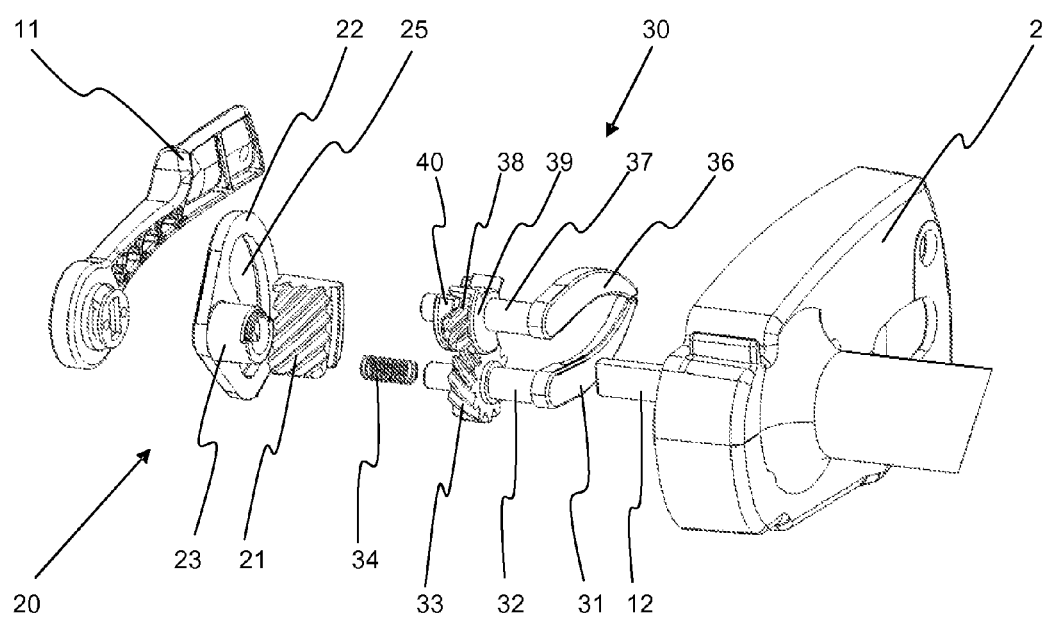
FIG. 1: an exploded view of the holding device according to the invention.

The holding device (1) according to the invention is constituted essentially by three main elements: a control member (10), a converting and transmitting device (20) and a mechanism for transferring the movement to the arm (30). The whole mechanism, with the exception of the arms, is enclosed in a housing formed by a cover (2) and a bottom (3).

The arms (31, 36) are placed each on an axis (32, 37) parallel to the axis of the syringe. Each of these arms carries a pinion having a helical set of teeth (33, 38). The sets of teeth of these pinions are preferably slanted at an angle of 45°. The two pinions (33, 38) are designed to cooperate with each other, the slanting direction of their sets of teeth being thus reversed. In order to make the two pinions (33, 38) integral in translation with each other, one of the two, here, the upper pinion (38), is equipped on its two lateral faces with a flange (39, 40). The lateral faces of the teeth of the lower pinion (33) are thus placed between the two flanges (39, 40), which forces the upper pinion (38) to move at the same time as the lower pinion (33).

Figure 3:
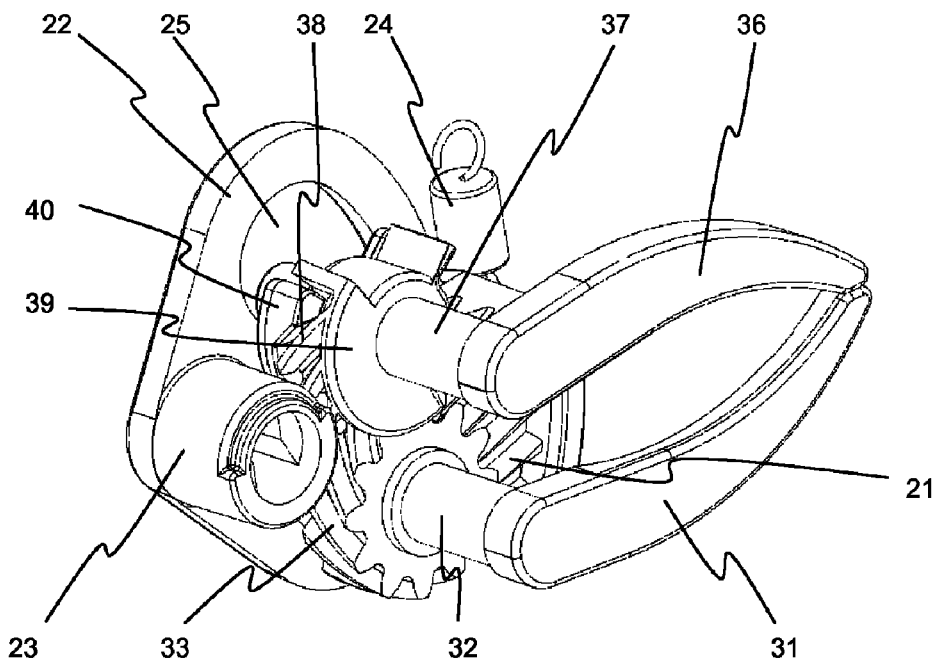
FIG. 3: a perspective view of the device of FIG. 2.
Figure 5:
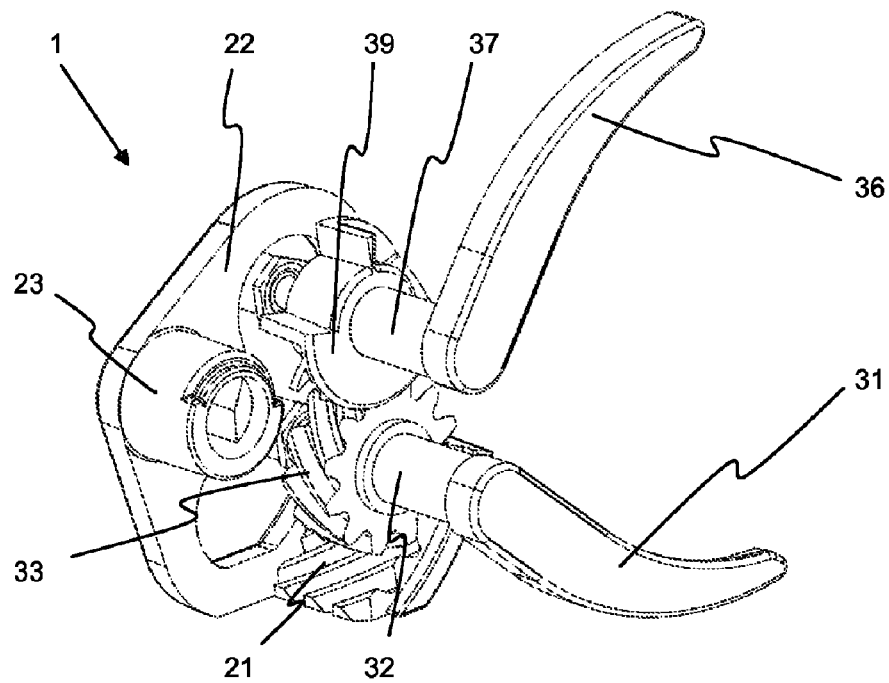
FIG. 5: a perspective view of the device of FIG. 4.

Further, the arms (31, 36) and thus the rotation axes (32, 37) can pivot in opposed directions (because the two pinions (33, 38) mesh with each other) between a "closed" position where the free ends of the arms (31, 36) touch each other (FIG. 3) and an "opened" position in which the arms (31, 36) are moved away from each other as much as possible (FIG. 5). The arms (31, 36) move from one position to the other as a result of a rotation of the pinions (33, 38) relative to each other. In other words, by pivoting the lower pinion (33), the upper pinion (38) is caused to pivot, which causes the arms (31, 36) to open or to close.

Figure 6:
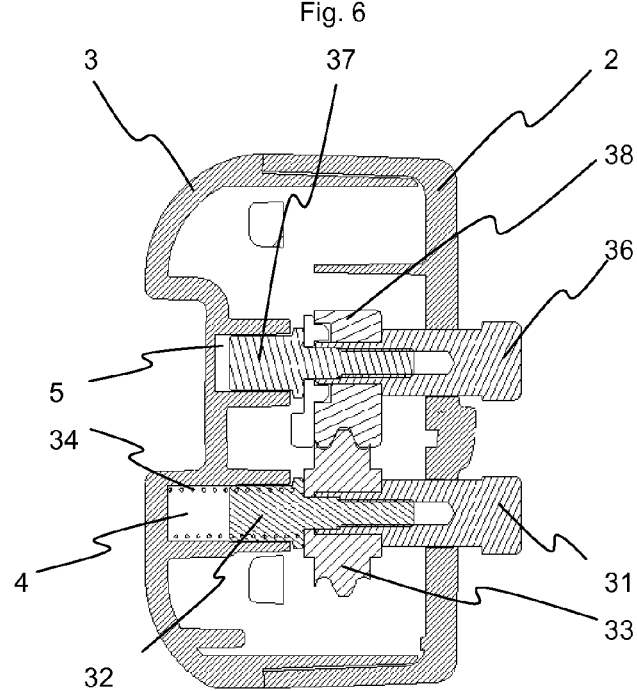
FIG. 6: a cross-sectional view of the device in the closed position according to FIG. 2.
Figure 7:
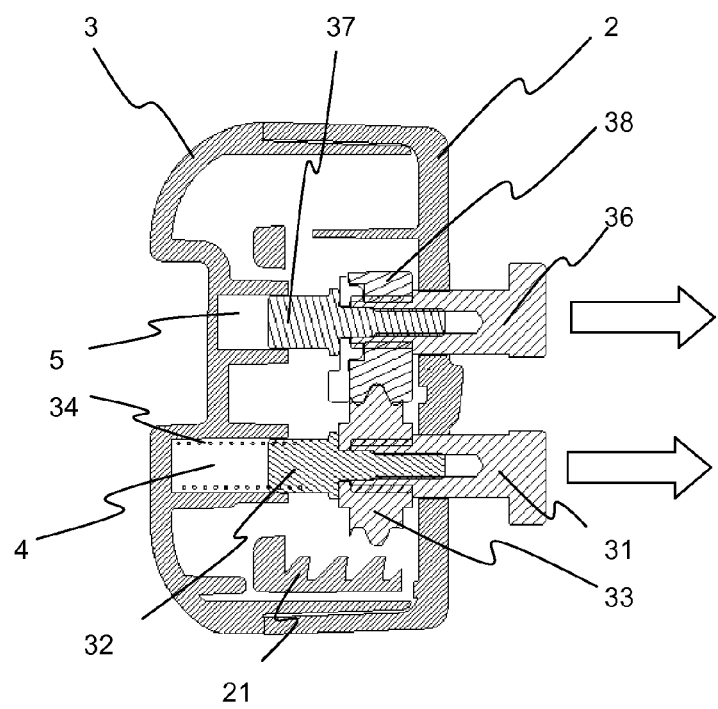
FIG. 7: a cross-sectional view of the device in the opened position according to FIG. 4.

The rotation axes (32, 37) of the arms (31, 36) are housed in the housing (2, 3) in cylindrical cavities (4, 5) provided in the bottom of the housing (3). The arms (31, 36) pass through corresponding openings provided in the cover of the housing (2). The cylindrical cavities (4, 5) and the corresponding openings are located so that the pinions (33, 38) mesh with each other. The arms/rotation axes assemblies (31/32, 36/37) can slide in the housing between a "pushed back" position (see FIG. 6) and a "drawn out" position (see FIG. 7). In the "pushed back" position, the arms (31, 36) are pushed against or nearly against the pusher, i.e., against the cover of the housing (2). In the embodiment shown, the rotation axes project into the cylindrical cavities (4, 5) at the bottom of the housing (3) and the pinions (33, 38) are supported against a first stop, for example, the edge of the cylindrical cavities (4, 5). In the "drawn out" position, the arms are in the position located farthest from the pusher, characterized by the fact that the pinions (33, 38) are supported against a second stop, for example, the cover (2) of the housing. A spring (34) tends to return the lower rotation axis (32) toward the "drawn out" position.

The converting and transmitting mechanism (20) is constituted essentially by a helical pinion segment having a helical inner set of teeth (21). This set of teeth is preferably slanted at an angle of 45°, like that of the pinions (33, 38). The helical set of teeth (21) is intended to cooperate with the lower pinion (33) of the lower arm (31). It is located on a support (22) having at its center a slot (25) that is sufficiently large to let the rotation axes (32, 37) carrying the arms (31, 36) pass freely through it. A very compact device is thus obtained. On the side opposed to the helical set of teeth (21), the support (22) is equipped with a ring (23) that is intended to receive the control member (10). The converting and transmitting mechanism pivots about the axis of this ring (23). This ring is housed in the housing (2, 3) so that it can pivot between two extreme positions while being locked in translation. A spring (24) tends to maintain or return the converting and transmitting mechanism toward its rest position (see FIG. 2). This position corresponds to the "pushed back" and "closed" position of the arms (31, 36). When the control member (10) transmits to the converting and transmitting device a rotation movement sufficiently strong to counter the action of the spring (24), this rotation movement is transmitted by the ring (23) to the support (22) and finally to the helical set of teeth (21). The latter moves until it reaches an extreme position corresponding to the "drawn out" and "opened" position of the arms (31, 36). The spring (24) is located preferably in tension between the housing (2) and a point close to the helical set of teeth (21).

The control member (10) can be constituted by a lever (11) and/or a control rod (12) controlled by the syringe pusher itself. It is thus possible to actuate the device either manually or in an automated manner, as one chooses. In both cases, the connection between the control member (10) and the transmission ring (23) is such that it allows the holding device not to return completely to its rest position, i.e., the arms being completely closed and completely pressed against the pusher. For this purpose, the control rod (12) is not completely integral with the ring (23). It can pivot in an opening (25) that provides a certain play, as will be explained below.

The holding device of the invention operates in the following manner: in the rest position, the spring (24) tends to return the helical set of teeth (21) toward the rest position. The lower pinion (33) meshes with the helical set of teeth so that it is pressed against the opening of the cylindrical cavity (4), similarly to the upper pinion (38), which is pressed against the opening of the cylindrical cavity (5). The spring (34) tends to return the lower pinion (33) toward the "drawn out" position, but the force of this push spring (34) is selected so that its action is weaker than the action of the return spring (24). The pinions (33, 38) are thus locked in the position in which the arms (31, 36) are pressed against the pusher (2). In this position, the arms (31, 36) are in "closed" position, i.e., their free ends touch each other (see FIG. 3).

Figure 2:
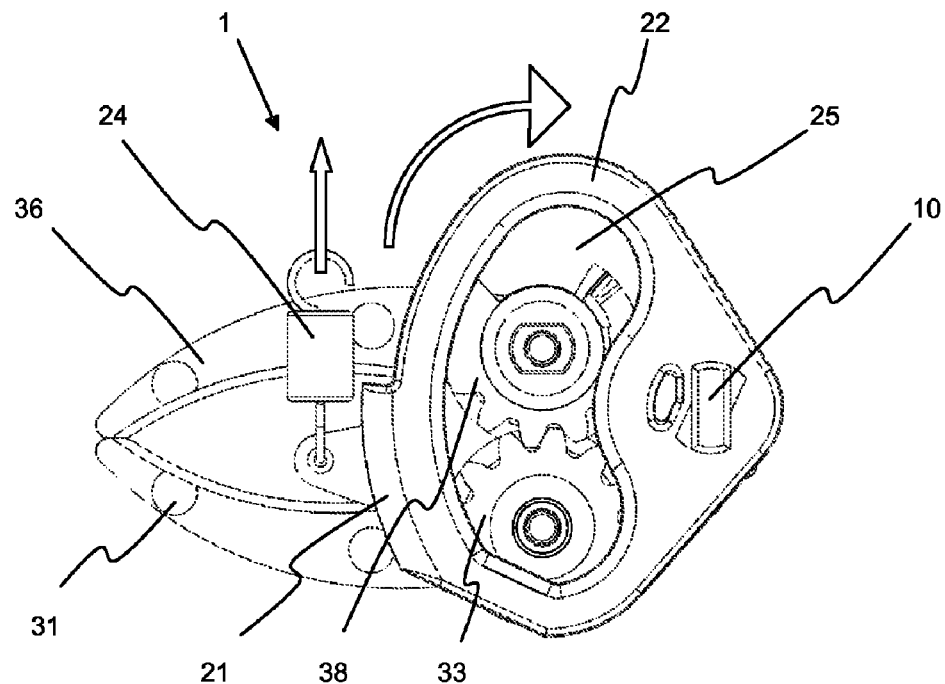
FIG. 2: a rear view of the device in the closed position.
Figure 4:
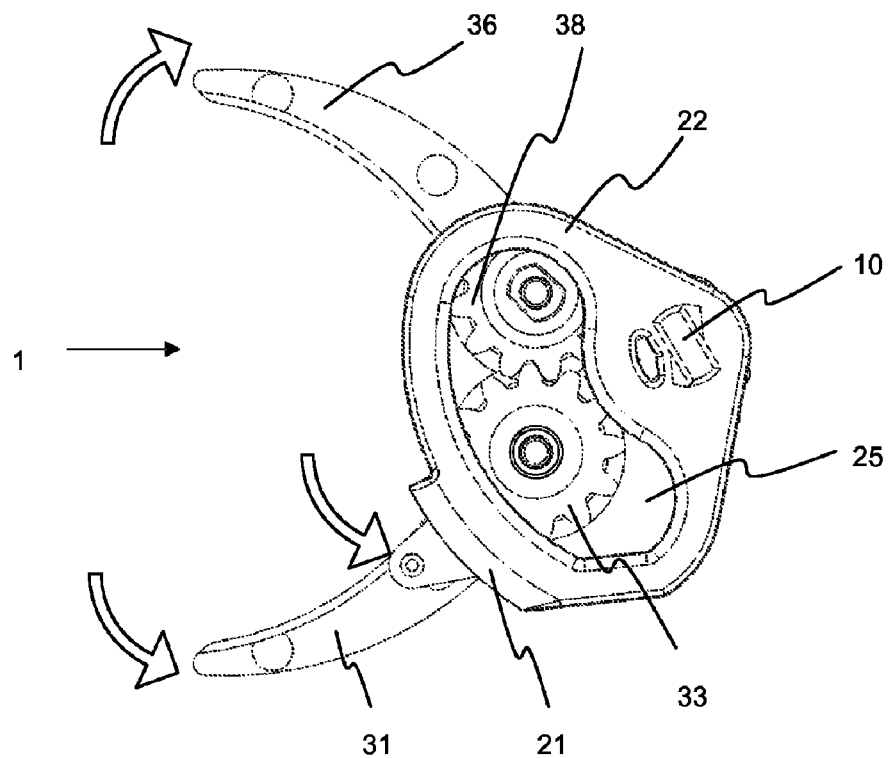
FIG. 4: a rear view of the device in the opened position.

When the control member (10) pivots in the direction opposed to the action of the return spring (24), the helical set of teeth pivots downward (as seen, for example, on FIGS. 2 and 4). It drives the lower pinion (33) that meshes with it. The push spring (34) tends to return the pinion (33) axially toward the "drawn out" position. The helical conformation of the sets of teeth of the pinions (21, 33) makes it possible, at first sight, either to convert the rotation movement of the helical pinion segment (21) into a translation movement of the lower pinion (33), or to transmit the rotation movement to the lower pinion (33). By choosing the force of the spring (34) so that its action is stronger than the friction forces caused by the sliding movement of the teeth of the lower pinion against the set of teeth of the helical pinion segment, the translation movement is promoted, as compared to the rotation movement. The lower pinion (33) will thus move in translation along its rotation axis until it becomes blocked against a stop, for example, the cover (2) of the housing.

Once it has reached this position, the rotation movement of the helical pinion segment can no longer be converted into a translation movement: it is thus transmitted to the lower pinion (33) in the form of a rotation. Thus, the lower pinion (33) performs at first a translation movement, then a rotation movement. The lower arm (31) with which it is integral thus performs a movement that moves it away from the pusher (2) until it reaches its "drawn out" position, then moves it away from its closed position until it reaches its "opened" position.

The upper pinion (38) being integral in translation with the lower pinion (33) because of the flanges (39, 40) that hold tightly the teeth of the latter, it performs at first the same translation movement, then the same rotation movement, but in the opposed direction. The upper arm (36) is thus, at first, moved away from the pusher, then moved away from its closed position in the direction opposed to the movement of the lower arm (31).

When the control member returns to the rest position, the spring (24) tends to return the helical pinion segment (21) toward the rest position by pivoting it upward (with respect to FIGS. 2 and 4). Since the spring (34) tends to maintain the pinion (33) in the "drawn out" position, the pivoting movement of the helical pinion segment (21) causes the lower pinion (33) to pivot, the upper pinion (38) thus pivoting in correspondence. This results in returning the arms (31, 36) toward the closed position until they reach the piston rod of the syringe (if it is sufficiently thick) or until their free ends touch each other in the "closed" position. In both cases, the rotation movement of the pinions (33, 38) is locked. The rotation movement of the helical pinion segment (21) is then converted into a translation movement of the lower pinion (33) with respect to the helical pinion segment (21) against the action of the push spring (34). As a result of this translation movement, the arms reenter the housing (2) until they become blocked against the piston head of the syringe. In this position, which does not correspond exactly to the rest position, the rotation of the helical pinion segment is locked. In order to avoid damaging the device, it is thus preferable to provide a play in the transmission ring (23) that enables the control member (10) to return to its rest position even when the holding device itself is not in its rest position. When the control device begins a new rotation movement, for example, in order to free the syringe piston head, the start of this rotation movement will have no effect on the helical pinion segment and thus on the arms.

The device according to the invention thus comprises very few parts, among which only a very small number is subjected to a translation movement. The holding device of the invention is thus much more reliable and sturdy in use, and its manufacturing cost can be reduced, as compared to the devices of the state of the art.

Instead of a helical pivot (21/22), it is also possible to provide a planar helical set of teeth, which is subjected, not to a rotation movement, but to a translation movement parallel to its main plane. Similarly, it is possible to locate the helical set of teeth (21), not toward the inside of the pivot (22), but toward the outside, by placing the pinions integral with the arms outside of the pivot (22). However, such a device is less compact than the one described before.

LIST OF REFERENCES

1 Holding device
2 Housing cover
3 Housing bottom
4 Lower cylindrical cavity
5 Upper cylindrical cavity
10 Control member
11 Manual control lever
12 Automatic control rod
20 Converting and transmitting device
21 Helical set of teeth
22 Support
23 Ring
24 Return spring
25 Slot
30 Movement transmitting device
31 Lower arm
32 Lower rotation axis
33 Lower pinion
34 Push spring
36 Upper arm
37 Upper rotation axis
38 Upper pinion
39 Flange
40 Flange

The invention claimed is:

1. Holding device for locking the piston head of a syringe on the pusher of a syringe pump, comprising:
  arms integral each with a pinion pivotable about its axis and movable in translation so as to drive the corresponding arm in a same movement between a rest position in which the arms are "closed" and "pressed" against the pusher and an open position in which the arms are "opened" and "removed" from the pusher, the translation being performed before the rotation during the movement toward the open position or in reverse order toward the rest position,
  a control member, and
  (i) first means for converting a portion of the movement of the control member by transmitting it to at least one of the pinions in the form of a translation movement and (ii) second means for converting a portion of the movement of the control member by transmitting it to the at least one pinion in the form of a rotation movement,
  wherein the means for converting and transmitting a portion of the movement of the control member into a translation movement of the at least one pinion are locked in translation,
  wherein the first and second means are constituted by means for conveying both a translation movement and a rotation movement to the at least one pinion in the movement toward the open position and in the movement toward the closed position,
  wherein the translation movement is promoted over the rotation movement in the movement toward the open position and the rotation movement is promoted over the translation movement in the movement toward the rest position.

2. Device according to claim 1, wherein the pinions integral with the arms mesh with each other so that the rotation of one of the pinions causes the rotation of the other pinion in the opposed direction.

3. Device according to claim 2, wherein one of the pinions is equipped on its lateral faces with flanges to make the two pinions integral with each other in translation.

4. Holding device according to claim 1, wherein the means for converting and transmitting a portion of the movement of the control member into a translation movement of at least one pinion and the means for converting and transmitting a portion of the movement of the control member into a rotation movement of at least one pinion are constituted by a helical set of teeth.

5. Device according to claim 4, wherein the pinion that cooperates with the converting and transmitting means is equipped with a helical set of teeth compatible with the helical set of teeth of the converting and transmitting means, and in that the two helical sets of teeth cooperate with each other.

6. Device according to claim 5, wherein the two pinions integral with the arms are equipped with reversed helical sets of teeth.

7. Device according to claim 4, wherein the helical sets of teeth are slanted at an angle of about 45°.

8. Device according to claim 1, wherein pushing means are provided to push at least one of the pinions toward a removed position.

9. Device according to claim 1, wherein return means are provided to return the holding device to the rest position or to a position as close as possible to this extreme position, in which the arms are as closed as possible and as close as possible to the pusher.

10. Holding device according claim 8, wherein return means are provided to return the holding device to the rest position or to a position as close as possible to this extreme position, in which the arms are as closed as possible and as close as possible to the pusher, and wherein the action of the return means is stronger than the action of the pushing means so that the device tends to return to the rest position when the control member is not in action.

11. Holding device according to claim 1, wherein the control member is integral with an external control lever and/or transmitting means controlled by the syringe pump.

12. Holding device according to claim 1, wherein means are provided to enable the control member to return to the rest position even if the holding device remains locked in an intermediary position between the open position and the rest position.

13. Holding device according to claim 4, wherein the set of teeth are located toward the inside of the pinion.

14. Device according to claim 13, wherein the sets of teeth mesh with each other.

15. Device according to claim 5, wherein the sets of teeth mesh with each other.

16. Device according to claim 4, wherein the helical set of teeth are mounted on a Pinion.

17. Device according to claim 8, wherein the pushing means are constituted by a push spring.

18. Device according to claim 8, wherein the action of the pushing means is sufficiently strong to promote, in the direction of opening and moving the arms away, the translation movement of the pinions, as compared to their rotation movement.

19. Holding device according claim 8, wherein return means are provided to return the holding device to the rest position or to a position as close as possible to this extreme position, in which the arms are as closed as possible and as close as possible to the pusher, and wherein the action of the return means is stronger than the action of the pushing means so that the device tends to return to the rest position when the control member is not in action.

20. Holding device according to claim 1, wherein the device comprises pushing means for pushing the at least one pinion toward the removed position, so that the translation movement is promoted over the rotation movement during the movement toward the open position and the rotation movement is promoted over the translation movement during the movement toward the rest position.

* * * * *